(12) United States Patent
Ventura et al.

(10) Patent No.: US 10,060,253 B2
(45) Date of Patent: Aug. 28, 2018

(54) DOWNHOLE SYSTEMS AND ARTICLES FOR DETERMINING A CONDITION OF A WELLBORE OR DOWNHOLE ARTICLE, AND RELATED METHODS

(71) Applicant: Baker Hughes Incorporated, Houston, TX (US)

(72) Inventors: Darryl N. Ventura, Houston, TX (US); Rostyslav Dolog, Houston, TX (US); Valery N. Khabashesku, Houston, TX (US); Nicholas Carrejo, Katy, TX (US); Kevin Holmes, Houston, TX (US); Thomas McClain Scott, Cypress, TX (US); Xiuli Wang, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 195 days.

(21) Appl. No.: 15/095,884

(22) Filed: Apr. 11, 2016

(65) Prior Publication Data
US 2017/0292366 A1 Oct. 12, 2017

(51) Int. Cl.
*E21B 47/10* (2012.01)
*E21B 33/12* (2006.01)
*G01N 27/04* (2006.01)

(52) U.S. Cl.
CPC .......... *E21B 47/102* (2013.01); *E21B 33/12* (2013.01); *E21B 33/1208* (2013.01); *G01N 27/04* (2013.01); *Y02A 90/342* (2018.01)

(58) Field of Classification Search
CPC ........ G01N 27/04; E21B 47/102; E21B 33/12
See application file for complete search history.

(56) References Cited

U.S. PATENT DOCUMENTS

| | | |
|---|---|---|
| 7,743,835 B2 | 6/2010 | Willauer |
| 7,924,031 B2 | 4/2011 | Watkins, Jr. et al. |
| 8,118,092 B2 | 2/2012 | Korte et al. |
| 8,181,708 B2 | 5/2012 | Korte et al. |
| 8,225,861 B2 | 7/2012 | Foster et al. |

(Continued)

FOREIGN PATENT DOCUMENTS

WO 2015077524 A1 5/2015

OTHER PUBLICATIONS

John, Gerald Francis, Towards Improved Application of Super Absorbent Polymers in Agriculture and Hydrology: A Cross-Disciplinary Approach, A thesis sumitted to the Graduate Faculty of Auburn University, Dec. 12, 2011, 64 pages.

(Continued)

*Primary Examiner* — Michael R Wills, III
(74) *Attorney, Agent, or Firm* — TraskBritt

(57) ABSTRACT

A method of determining a condition within a wellbore. The method comprises introducing a tubular member in a wellbore extending through a subterranean formation, the tubular member comprising a downhole article including a deformable material disposed around a surface of the tubular member, electrically conductive elements dispersed within the deformable material. The method includes measuring at least one electrical property of the deformable material. At least one of water ingress into the wellbore or an amount of expansion of the deformable material is determined based on the at least one measured electrical property. Related downhole systems and other related methods are also disclosed.

20 Claims, 5 Drawing Sheets

(56) References Cited

U.S. PATENT DOCUMENTS

| | | | |
|---|---|---|---|
| 8,684,075 B2 | 4/2014 | Guest et al. | |
| 8,943,884 B2 | 2/2015 | Kumar | |
| 9,090,012 B2 | 7/2015 | Mazyar et al. | |
| 9,228,420 B2 | 1/2016 | Mazyar et al. | |
| 9,637,996 B2 * | 5/2017 | DiFoggio | E21B 33/13 |
| 2004/0065436 A1 | 4/2004 | Schultz et al. | |
| 2006/0253942 A1 * | 11/2006 | Barrera | B82Y 15/00 73/661 |
| 2008/0173111 A1 | 7/2008 | Thostenson et al. | |
| 2008/0220991 A1 * | 9/2008 | Slay | E21B 33/1208 507/203 |
| 2009/0120689 A1 | 5/2009 | Zaeper et al. | |
| 2009/0139708 A1 | 6/2009 | Foster | |
| 2011/0089958 A1 | 4/2011 | Malecki et al. | |
| 2011/0192598 A1 | 8/2011 | Roddy et al. | |
| 2012/0017674 A1 | 1/2012 | Kumar | |
| 2012/0118558 A1 | 5/2012 | Yoshiuchi et al. | |
| 2012/0142111 A1 | 6/2012 | Tour et al. | |
| 2012/0208934 A1 | 8/2012 | Korte et al. | |
| 2012/0292023 A1 | 11/2012 | Hinkle et al. | |
| 2012/0312523 A1 | 12/2012 | Joseph et al. | |
| 2012/0312560 A1 | 12/2012 | Bahr et al. | |
| 2013/0062067 A1 * | 3/2013 | Guest | B82Y 30/00 166/309 |
| 2014/0102728 A1 | 4/2014 | Gamstedt et al. | |
| 2015/0037895 A1 | 2/2015 | Lobez Comeras | |
| 2015/0176363 A1 | 6/2015 | Mazyar et al. | |
| 2015/0210825 A1 | 7/2015 | Sadana et al. | |
| 2017/0254170 A1 * | 9/2017 | Mazyar | E21B 33/1208 |
| 2017/0254194 A1 * | 9/2017 | Mazyar | E21B 47/122 |

OTHER PUBLICATIONS

Kim et al., Paper Actuators Made with Cellulose and Hybrid Materials, Sensors, vol. 10, (2010), pp. 1473-1485.
Mazyar et al., Deformable Downhole Structures Including Carbon Nanotube Materials, and Methods for Forming and Using Such Structures, U.S. Appl. No. 15/063,034, filed Mar. 7, 2016.
Qi et al., Unique Water Sensors Based on Carbon Nanotube-Cellulose Composites, Sensors and Actuators B: Chemical, vol. 185, (2013), pp. 225-230.
International Search Report for International Application No. PCT/US2017/026763 dated Jul. 20, 2017, 3 pages.
International Written Opinion for International Application No. PCT/US2017/026763 dated Jul. 20, 2017, 7 pages.

* cited by examiner

DOWNHOLE SYSTEMS AND ARTICLES FOR DETERMINING A CONDITION OF A WELLBORE OR DOWNHOLE ARTICLE, AND RELATED METHODS

TECHNICAL FIELD

Embodiments of the disclosure relate generally to materials for monitoring a condition of a wellbore or of a downhole article disposed within the wellbore, and related methods. More particularly, embodiments of the disclosure relate to deformable or degradable downhole articles including electrically conductive materials dispersed therein, and methods of forming and using such deformable downhole articles.

BACKGROUND

The drilling of wells for oil and gas production conventionally employs longitudinally extending sections or so-called "strings" of drill pipe to which, at one end, is secured a drill bit of a larger diameter. After a selected portion of a wellbore has been drilled, and in some instances reamed to a larger diameter than that initially drilled with a drill bit (which in such instances is termed a "pilot" bit), the wellbore is usually lined or cased with a string or section of casing or liner. Such a casing or liner exhibits a larger diameter than the drill pipe used to drill the wellbore, and a smaller diameter than the drill bit or diameter of a reamer used to enlarge the wellbore. Conventionally, after the casing or liner string is placed in the wellbore, the casing or liner string is cemented into place to form a seal between the exterior of the casing or liner string and the wellbore wall.

Tubular strings, such as drill pipe, casing, or liner, may be surrounded by an annular space between the exterior wall of the pipe and the interior wall of the well casing or the wellbore wall. Frequently, it is desirable to seal such an annular space between upper and lower portions of the well depth or between adjacent horizontal zones of the well. The annular space may be sealed or filled with a downhole article, such as a conformable device. Conformable devices include packers, bridge plugs, sand screens, and seals. Swellable packers and bridge plugs are particularly useful for sealing an annular space because they swell (e.g., expand) upon exposure to wellbore fluids, wellbore temperatures, and the like and fill the cross-sectional area of the annular space.

However, such deformable materials are sometimes ineffectively placed and set in the wellbore and, therefore, do not operate as intended. For example, a deformable material may not substantially expand and form a complete seal between the tubular member and the wellbore wall. In other embodiments, a swellable packer may either degrade after a useful life and may not, therefore, effectively seal across the annular space. Such malfunctions may cause flow of formation fluids from different zones to undesirably mix, be produced at the surface, or both.

Other downhole tools and components are often exposed to aggressive environments that may corrode or degrade such tools and components. For example, downhole tools may be exposed to high temperatures and high pressures, acid gases (e.g., $H_2S$, $CO_2$), and solutions of varying composition, pH, salinity, which exposure may lead to pitting, corrosion, or degradation of the downhole tool or component. Often, a downhole tool or component may degrade unbeknownst to an operator of the wellbore.

BRIEF SUMMARY

Embodiments disclosed herein include downhole systems for determining at least one condition within a wellbore, as well as related methods. For example, in accordance with one embodiment, a method of determining a condition within a wellbore or a downhole article comprises introducing a tubular member in a wellbore extending through a subterranean formation, the tubular member comprising a downhole article including a deformable material disposed over a surface of the tubular member, the deformable material having electrically conductive nanomaterials dispersed therein, measuring at least one electrical property of the deformable material, and determining at least one of water ingress into the wellbore or an amount of expansion of the deformable material based on a value of the at least one measured electrical property.

In additional embodiments, a downhole system for determining at least one condition within a wellbore comprises a tubular member in a wellbore extending through a subterranean formation, a deformable material disposed over a surface of the tubular member, the deformable material comprising electrically conductive nanomaterials dispersed therein, at least one electronic device electrically coupled to electrodes within the deformable material, the electronic device configured to measure at least one electrical property of the deformable material, and a processor operably coupled to the at least one electronic device, the processor comprising a memory programmed to determine at least one of water ingress into the wellbore or an amount of expansion of the deformable material based on a value of the at least one measured electrical property.

In further embodiments, a method of determining an amount of degradation of a downhole tool comprises positioning a tubular member in a wellbore, the tubular member comprising a degradable material disposed around a surface of the tubular member and comprising a plurality of electrically conductive elements therein, measuring at least one electrical property of each of the electrically conductive elements, and determining an amount of degradation of the degradable material based, at least in part, on a value of the at least one measured electrical property of each of the electrically conductive elements.

DETAILED DESCRIPTION

Figure 1:
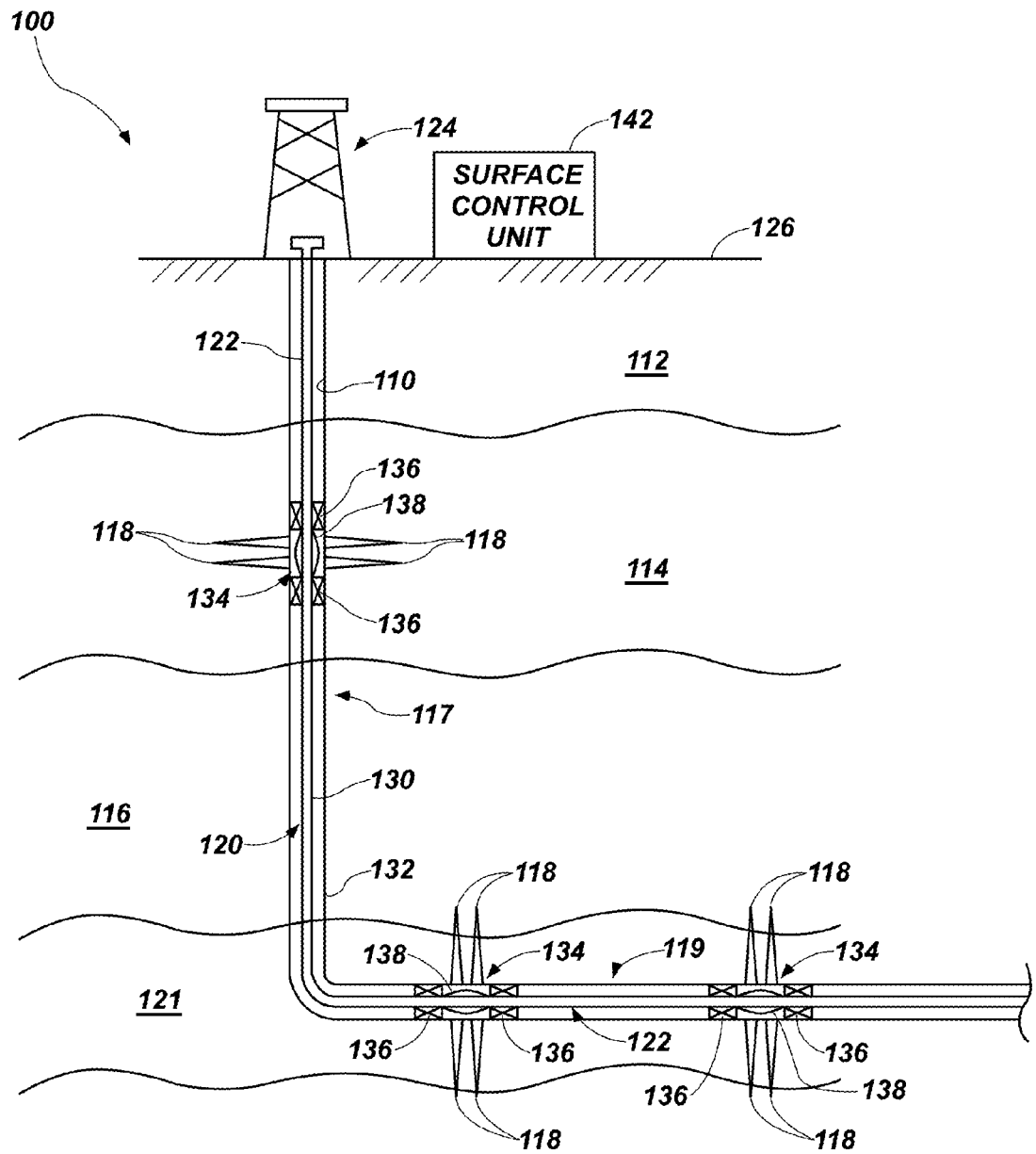
FIG. 1 is a schematic diagram of a wellbore system including at least one deformable downhole article disposed therein.

Illustrations presented herein are not meant to be actual views of any particular material, component, or system, but are merely idealized representations that are employed to describe embodiments of the disclosure.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for forming a deformable material or forming a degradable material, an article including the deformable material or the degradable material, or methods of operating a wellbore with such materials. Only those process acts and structures necessary to understand the embodiments of the disclosure are described in detail below. A person of ordinary skill in the art will understand that some process components (e.g., pipelines, line filters, valves, temperature detectors, flow detectors, pressure detectors, and the like) are inherently disclosed herein and that adding various conventional process components and acts would be in accord with the disclosure. Additional acts or materials to form a seal between at least a component of a downhole tool and a wellbore wall and to determine a condition of the wellbore or downhole article may be performed by conventional techniques.

Methods and downhole tools and articles as described herein may be used for detecting one or more of a condition of a downhole article including a deformable material (e.g., a swellable packer, a deformable material such as a sand screen, etc.) or a degradable material, as well as a wellbore associated with the downhole article, such as, for example, an amount of expansion or contraction of such downhole articles, an amount of degradation of such articles, or water ingress into the wellbore proximate the article. According to embodiments described herein, deformable downhole articles may be formed of a deformable material and an electrically conductive material (e.g., carbon nanotubes, carbon nanotube mats, etc.) dispersed throughout the deformable material. According to other embodiments, a degradable downhole article may be formed of a degradable material and an electrically conductive material or electrically conductive elements disposed therein. Responsive to exposure to one or more types of a predetermined fluid or predetermined conditions (e.g., temperature, pressure, salinity, pH, etc.), the deformable material or degradable material may expand and alter at least one electrical property (e.g., an electrical resistance) of the material. Accordingly, an electrical resistance through the material may be correlated to a condition of the downhole article including the material.

As used herein, the term "deformable material" means and includes any material that may swell, expand, or otherwise increase in size in at least one dimension or direction responsive to exposure to a downhole environment or stimulus. By way of nonlimiting example, the downhole environment or stimulus may include a fluid having a predetermined property (e.g., polarity, salinity, pH, etc.), a temperature, pressure, an electrical stimulus, or other property.

As used herein, the term "degradable material" means and includes any material that may degrade, corrode, erode, or otherwise deteriorate chemically, physically, or by any other means responsive to exposure to a downhole environment or stimulus. By way of nonlimiting example, the downhole environment or stimulus may include a fluid having a predetermined property (e.g., polarity, salinity, pH, etc.), a temperature, pressure, an electrical stimulus, or other property.

FIG. 1 is a schematic diagram of a wellbore system 100 including a wellbore 110 extending through a subterranean formation, which may include an aquifer zone 112 and one or more producing reservoirs 114, 116, 121 including, for example, hydrocarbons. In some embodiments, at least a portion of the wellbore 110 may be lined with a casing. The wellbore 110 may include a substantially vertical leg 117 and a deviated, or substantially horizontal leg 119. The wellbore 110 may include a production string or assembly, generally indicated at 120, including a tubular component 122 disposed therein. The tubular component 122 may extend downwardly from a drill rig 124 at a surface 126 of the subterranean formation and through the wellbore 110. An annulus 130 may be defined between an outer wall of the tubular member 122 and the wellbore casing and cement between the casing and a wellbore wall 132.

A number of perforations 118 may penetrate the wellbore casing and wellbore wall 132 and extend into the subterranean formation, such as at the producing reservoirs 114, 116, 121. Production zones 134 may be positioned at selected locations along the production assembly 120, such as proximate one or more perforations 118. Each production zone 134 may be isolated within the wellbore 110 by a pair of packer devices 136. Although FIG. 1 illustrates only three production zones 134, the wellbore system 100 may include a greater number of such zones arranges in serial fashion along one or both of the vertical leg 117 and horizontal leg 119.

Each production zone 134 may include a flow control device 138 to govern one or more aspects of a flow of one or more fluids into the production assembly 120 (e.g., the tubular component 122). As used herein, the term "fluid" or "fluids" includes liquids, gases, hydrocarbons, multi-phase fluids, mixtures of two or more fluids, water, brine, engineered fluids such as drilling mud, fluids injected from the surface such as water, and naturally occurring fluids such as oil and gas.

At least one component of the tubular component 122 or the production string 120 may be formed of a degradable material formulated and configured to degrade responsive to exposure to one or more predetermined conditions. By way of nonlimiting example, the one or more predetermined conditions may include exposure to a fluid having a predetermined property (e.g., polarity, salinity, pH, etc.), a temperature, pressure, an electrical stimulus, or other property.

Figure 2A:
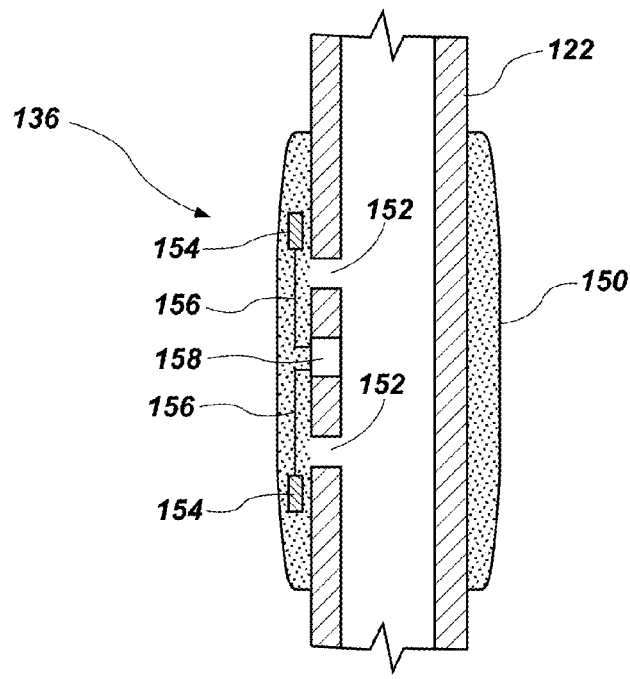
FIG. 2A is a cross-sectional side view illustrating a deformable downhole article in a compressed state, according to embodiments of the disclosure.

FIG. 2A is a cross-sectional side view of a packer device 136 of the wellbore system 100 of FIG. 1 in an initial, un-swollen configuration. The packer device 136 may include a deformable downhole article including a deformable material 150 disposed around an outer surface of a portion of the tubular component 122 in an initial, compressed configuration in which the deformable material 150 has a smaller diameter than a diameter of the wall 132 (FIG. 1) of the wellbore 110 or the wellbore casing, if present.

The deformable material 150 may be disposed around and substantially surround a section of the tubular component 122 within the wellbore 110. The tubular component 122 may be a portion of a downhole production pipe or tubing, or other, separate tubular component within the wellbore 110. The tubular component 122 may comprise plurality of orifices 152 configured to provide a flow of production fluids from the producing reservoir 114 through the production assembly 120, although the disclosure is not so limited and the tubular component 122 may not include any orifices 152 between two of the packer devices 136, if that reservoir 114 is not being produced.

The deformable material 150 may comprise one or more electrically conductive materials disposed therein. The deformable material 150 may further include electrodes 154 disposed therein. The electrodes 154 may comprise a suitable conductive material, such as, for example, nickel, tungsten, titanium, silver, graphite, other electrically conductive materials, or combinations thereof. Although FIG. 2A illustrates the electrodes 154 disposed within the deformable material 150, in other embodiments, the electrodes 154 may be disposed on, for example, a surface of the deformable material 150.

The electrodes 154 may be operably coupled to an electronic device 158 by one or more electrical leads or wires 156. The electronic device 158 may be disposed within the packer device 136, such as within a recess or other receptacle within the tubular member 122. The electronic device 158 may, responsive to signals from electrodes 154, be configured to measure at least one electrical property of the deformable material 150 during use and operation of the packer device 136. In some embodiments, the electrical device 158 comprises a multimeter or voltmeter.

The electronic device 158 may be operably coupled to a controller, such as the surface control unit 142 (FIG. 1). In some embodiments, the electronic device 158 is configured to transmit information relating to the measured electrical property to the surface 126 (FIG. 1) for analysis. In some embodiments, the electronic device 158 communicates with the surface control unit 142 by, for example, mud pulse telemetry, a wired connection extending through a wall of the tubular member 122, or by other conventional uplink/ downlink apparatus. Although FIG. 2A illustrates the electronic device 158 disposed in a wall of the tubular member 122, the disclosure is not so limited. For example, in other embodiments, the electronic device 158 may be located in another component of the production assembly 120 (FIG. 1), such as in another sub in the production assembly 120. In yet other embodiments, the electronic device 158 may be located at the surface 126 (FIG. 1).

Figure 2B:
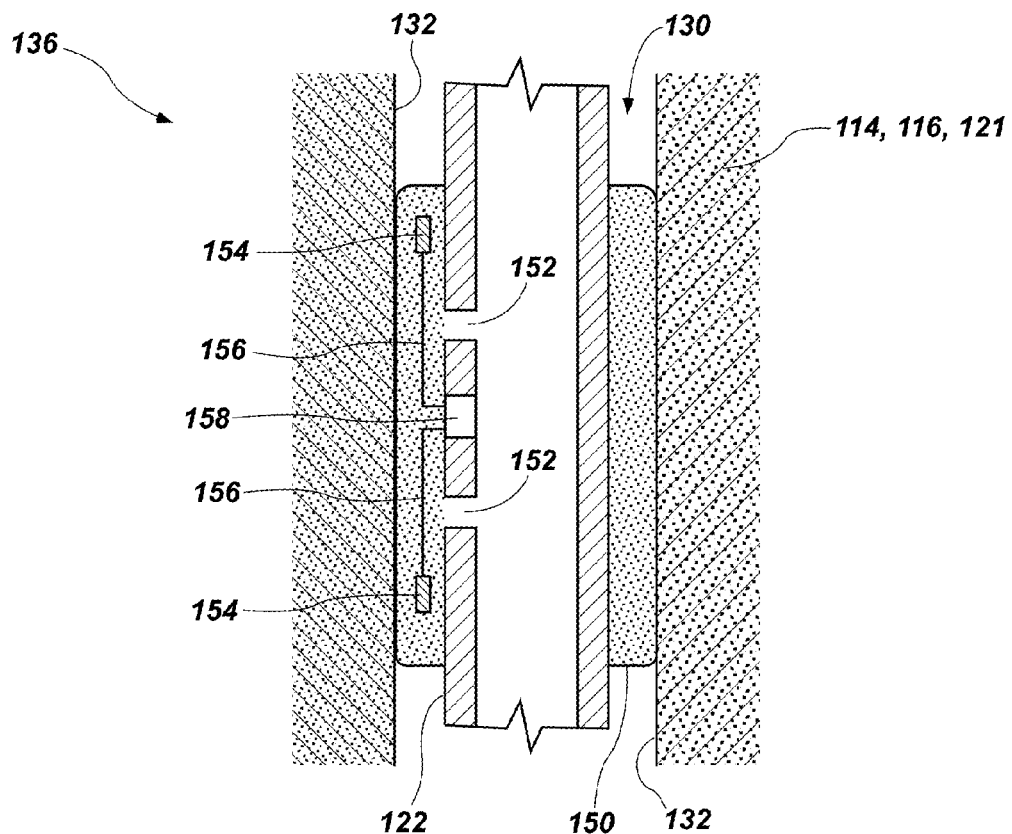
FIG. 2B is a cross-sectional side view illustrating the deformable downhole article of FIG. 2A in an expanded state, according to embodiments of the disclosure.

Referring to FIG. 2B, the deformable material 150 may be formulated and configured to expand until it substantially fills the annular space 130 after the tubular member 122 including the deformable material 150 is positioned within the wellbore 110 at a selected position. The packer device 136 may be positioned within the wellbore 110 while the deformable material 150 is in an initial, un-swollen state in which the deformable 150 has a smaller diameter than the diameter of the wall 132 of the wellbore 110 (FIG. 1). Swelling of the deformable material 150 may result in an increase in a radius of the deformable material 150 (measured from the tubular component 122 to an outer surface of the deformable material 150) by between about 20% and about 300% of an initial radius of the deformable material 150. In some embodiments, the initial radius of the deformable material 150 may be between about 0.5 inch (1.27 cm) to about 2 inches (5.08 cm). In some embodiments, the initial radius of the deformable material 150 is about 1 inch (2.54 cm).

In some embodiments, the deformable material 150 may be formulated and configured such that the deformable material 150 contacts the wall 132 of the wellbore 110 prior to fully expanding. In some such embodiments, the deformable material 150 may form a seal in the annulus 130 between the outer wall of the tubular member 122 and the wall 132 of the wellbore 110, may exhibit a pressure on the wall 132, and may stabilize the subterranean formation proximate the wellbore 110.

In some embodiments, the deformable material 150 may comprise an expandable material formulated and configured to expand responsive to exposure to one or more of a fluid having a predetermined property (e.g., polarity, salinity, pH, etc.), a temperature, pressure, or other property.

The deformable material 150 may include any suitable type of deformable material. By way of nonlimiting examples, the deformable material 150 may comprise a conformable material as described in any of U.S. Pat. No. 9,090,012, titled "PROCESS FOR THE PREPARATION OF CONFORMABLE MATERIALS FOR DOWNHOLE SCREENS," issued Jul. 28, 2015; U.S. Pat. No. 8,684,075, titled "SAND SCREEN, EXPANDABLE SCREEN AND METHOD OF MAKING," issued Apr. 1, 2014; U.S. Pat. No. 9,228,420, titled "CONFORMABLE MATERIALS CONTAINING HEAT TRANSFER NANOPARTICLES AND DEVICES MADE USING SAME," issued Jan. 5, 2016; and U.S. Pat. No. 9,428,985, titled "SWELLABLE DOWNHOLE STRUCTURES INCLUDING CARBON NITRIDE MATERIALS, AND METHODS OF FORMING AND USING SUCH STRUCTURES," issued Aug. 30, 2016, the entire disclosure of each of which is hereby incorporated herein by this reference. Such conformable materials may be used in conformable sand screens, such as the GEOFORM® conformable sand management system commercially available from Baker Hughes Incorporated of Houston, Tex. By way of further nonlimiting examples, the deformable material 150 may comprise a swellable material as described in any of U.S. Pat. No. 8,118,092, titled "SWELLING DELAY COVER FOR A PACKER," issued Feb. 21, 2012; U.S. Pat. No. 8,225,861, titled "SEALING FEED THROUGH LINES FOR DOWNHOLE SWELLING PACKERS," issued Jul. 24, 2012, U.S. Pat. No. 9,334, 337, titled "WATER SWELLING RUBBER COMPOUND FOR USE IN REACTIVE PACKERS AND OTHER DOWNHOLE TOOLS," filed Sep. 30, 2008; U.S. Patent Publication No. 2015/0210825, titled "ENHANCED WATER SWELLABLE COMPOSITIONS," issued May 10, 2016; U.S. Patent Publication No. 2009/0139708, titled "WRAP-ON REACTIVE ELEMENT BARRIER PACKER AND METHOD OF CREATING SAME," filed Jun. 6, 2008; and U.S. Pat. No. 8,181,708, titled "WATER SWELLING RUBBER COMPOUND FOR USE IN REACTIVE PACKERS AND OTHER DOWNHOLE TOOLS," issued May 22, 2012, the entire disclosure of each of which is hereby incorporated herein in their entirety by this reference.

By way of nonlimiting example, the deformable material 150 may comprise a polymer, a natural or synthetic rubber material, another elastomer, or another material. In some embodiments, the deformable material 150 comprises a polymer, such as a viscoelastic shape memory polymeric material. The shape memory polymeric material may exhibit a one-way shape memory effect such that the viscoelastic shape memory material may be restored to an original shape, size, or both when exposed to, for example, a change in temperature, wellbore fluids, electrical stimulus, a chemical stimulus, or other stimuli.

The polymer may include an open-celled foam material that can expand (e.g., exhibit a shape memory effect), such as, for example, a polyurethane, a polyamide, a polyurea, a polyvinyl alcohol, a vinyl alcohol-vinyl ester copolymer, a phenolic polymer, a polybenzimidazole, a copolymer comprising polyethylene oxide units, or combinations thereof. By way of nonlimiting example, copolymers comprising polyethylene oxide units include polyethylene oxide/acrylic acid/methacrylic acid copolymer crosslinked with N,N'-methylene-bis-acrylamide, polyethylene oxide/methacrylic acid/N-vinyl-2-pyrrolidone copolymer crosslinked with ethylene glycol dimethacrylate, and polyethylene oxide/poly(methyl methacrylate)/N-vinyl-2-pyrrolidone copolymer crosslinked with ethylene glycol dimethacrylate. In some embodiments, the deformable material 150 may include a polyurethane comprising a reaction product of a polycarbonate polyol and a polyisocyanate. Such polymers may be chemically or at least physically crosslinked in order to exhibit shape memory properties.

In other embodiments, the deformable material 150 may comprise an elastomeric material (e.g., rubber), as may be used in a swellable packer. The elastomeric material may be water-swellable (i.e., the elastomeric material may be configured and formulated to swell responsive to exposure to an aqueous solution) or oil-swellable (i.e., the elastomeric material may be configured and formulated to swell responsive to exposure to hydrocarbons).

The elastomeric material may include a rubber material such as natural rubber or a synthetic rubber copolymer. By way of nonlimiting example, the elastomeric material may include acrylonitrile butadiene styrene (ABS), polyacrylonitrile (PAN), a nitrile-based elastomer, such as acrylonitrile butadiene rubber (NBR, also known as Buna-N or PERBUNAN® and may include various grades thereof, such as hydrogenated acrylonitrile butadiene rubber (HNBR), carboxylated acrylonitrile butadiene rubber (XNBR), carboxylated hydrogenated acrylonitrile butadiene rubber (XH-NBR), and combinations thereof), ethylene propylene diene monomer (EPDM), fluorinated polymer rubbers (e.g., FKM), tetrafluoroethylene propylene rubbers (FEPM), fluorosilicone rubber, butyl rubbers, and combinations thereof.

The elastomeric material may be crosslinked. The crosslinks may include sulfur, peroxide, urethane, metallic oxides, boron oxide, acetoxysilane, alkoxysilanes, and combinations thereof. In some embodiments, the crosslinks comprise sulfur or a peroxide.

In some embodiments, such as where the elastomeric material is water-swellable, the elastomeric material comprises carboxymethyl cellulose (CMC) or a material comprising carboxymethyl cellulose. The carboxymethyl cellulose may include hydroxylpropylmethyl cellulose (HPMC), methylcellulose (MC), or a combination thereof. In some such embodiments, the elastomeric material may further include a mixture of an acrylic copolymer and a phthalate ester oil carrier dispersed in the elastomeric material. The acrylic copolymer may include a mixture of an active polymer and a phthalate ester oil and may include, for example, a material such as a Super Absorbent Polymer (SAP) (e.g., a long chain, slightly cross-linked polymer capable of absorbing relatively large quantities of liquid (e.g., water) relative to its own mass) and as described in U.S. Patent Application Publication No. U.S. 2012/0208934 A1, titled "WATER SWELLING RUBBER COMPOUND FOR USE IN REACTIVE PACKERS AND OTHER DOWNHOLE TOOLS," published Aug. 16, 2012, the entire disclosure of which is incorporated herein in its entirety by this reference.

As described above, the deformable material 150 may include an electrically conductive material therein. The electrically conductive material may be dispersed substantially uniformly throughout the deformable material 150. In other embodiments, the electrically conductive material may be dispersed in some portions of the deformable material 150 while other portions of the deformable material 150 are substantially free of the electrically conductive material. In some embodiments, the electrically conductive material may impart, at least to some degree, electrical conductivity to the deformable material 150, depending on, for example, an amount of contraction or expansion of the deformable material 150 and an electrical conductivity of the electrically conductive materials in the deformable material 150.

The electrically conductive material may include any material suitable for providing electrical conductivity to the deformable material 150. In some embodiments, an electrical conductivity (or similarly, an electrical resistance) of the deformable material 150 may correlate to an amount of expansion or contraction of the deformable material 150 including the electrically conductive material therein.

In some embodiments, the electrically conductive material may comprise any electrically conductive nanomaterial, such as electrically conductive carbon fibers or electrically conductive nanotubes. In some embodiments, the electrically conductive material comprises carbon nanotubes (CNTs). The carbon nanotubes may be single-walled carbon nanotubes, multi-walled carbon nanotubes, or a combination thereof. In some embodiments, the carbon nanotubes are multi-walled carbon nanotubes. In some embodiments, the electrically conductive material comprises one or more mats of carbon nanotubes. As used herein, the term "carbon nanotube mat" means and includes a sheet of carbon nanotubes including a plurality of randomly oriented carbon nanotubes, such as those commercially available from MER Corporation, of Tucson, Ariz. The carbon nanotube mats may have a thickness of between, for example, about 100 µm and about 500 µm, such as between about 100 µm and about 400 µm, or between about 200 µm and about 300 µm. However, the disclosure is not so limited and the carbon nanotube mats may have a different thickness.

The electrically conductive material may be functionalized. In some embodiments, the electrically conductive material comprises electrically conductive nanomaterials (e.g., carbon nanotubes) including one or more functional groups formulated and configured to facilitate bonding thereof to a portion of the deformable material 150. By way of nonlimiting example, the functional groups include amine groups, carboxyl groups (—COOH), thiol groups, fluorinated functional groups, hydroxyl groups, or combinations thereof. In some embodiments, the electrically conductive nanomaterials are functionalized to facilitate formation of the deformable material 150 including the electrically conductive nanomaterials therein.

The electrically conductive material may be doped (e.g., impregnated) with one or more dopants. In some such embodiments, the electrically conductive material comprises carbon nanotubes including metal nanoparticles attached to outer walls thereof. The nanoparticles may include, for example, at least one of platinum, copper, silver, gold, ruthenium, rhodium, tin, or palladium. In some embodiments, attachment of the metal nanoparticles to the carbon nanotubes may increase the electrical conductivity of the electrically conductive material thereof.

Figure 3A:
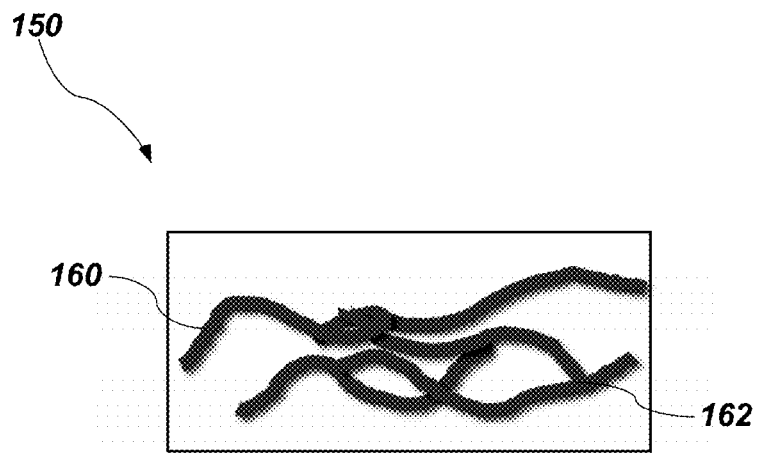
FIG. 3A and FIG. 3B are simplified schematics of a deformable material including carbon nanotubes therein, according to embodiments of the disclosure.
Figure 3B:
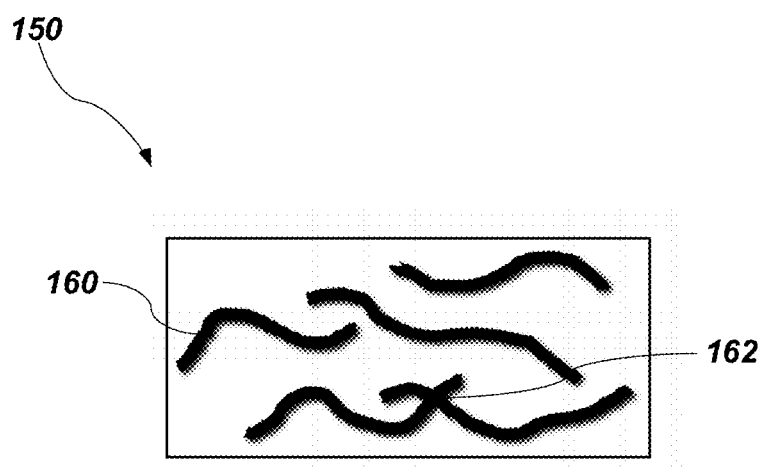

Referring to FIG. 3A, a schematic of the deformable material 150 is illustrated. The deformable material 150 may include electrically conductive nanomaterials 160, which may comprise, for example, a plurality of electrically conductive carbon nanotubes, dispersed therein. The electrically conductive nanomaterials 160 may include a plurality of electrically conductive junctions 162 at intersections between individual components (e.g., individual carbon nanotubes) of the electrically conductive nanomaterials 160. As used herein, the term "electrically conductive junction" means and includes a location where two or more individual components of the electrically conductive nanomaterials 160 physically contact each other. Electrons may flow through such electrically conductive junctions 162 rendering the electrically conductive junctions 162 and the electrically conductive nanomaterials 160 that are in physical contact with each other electrically conductive. The electrically conductive junctions 162 may form an electrically conductive network of electrically conductive nanomaterials 160 in the deformable material 150. An electrical conductivity and, therefore, an electrical resistance, of the deformable material 150 may be directly related to a number of electrically conductive junctions 162 within the deformable material 150. Referring to FIG. 3B, as the deformable material 150 expands, at least some of the electrically conductive junctions 162 may separate. Stated another way, expansion of the deformable material 150 may reduce a number of the electrically conductive junctions 162. Accordingly, since electrical conductivity through the deformable material 150 is through the electrically conductive nanomaterials 160 and the electrically conductive junctions 162, an electrical resistance through the deformable material 150 may substantially correspond to a degree of expansion or contraction of the deformable material 150.

Figure 4:
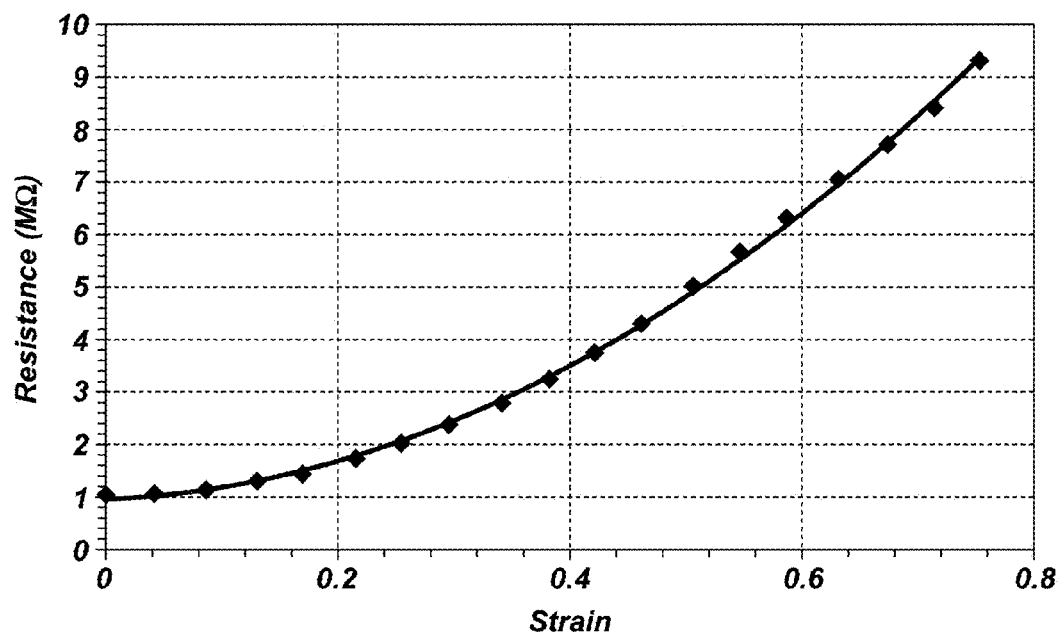
FIG. 4 is a graph illustrating a relationship between a measured resistance through a deformable material and a strain of the deformable material.

In use and operation, an amount of expansion or contraction of the deformable material 150 may be estimated or determined based on a measured electrical property of the deformable material 150. Referring to FIG. 4, a graph illustrating a relationship between a measured resistance through the deformable material 150 and a strain (i.e., an amount of deformation in a direction of an applied force divided by an initial dimension (length)) of the deformable material 150 is shown. As illustrated, a measured electrical resistance through the deformable material 150 may substantially correlate to an amount of strain of the deformable material 150. Accordingly, a degree of expansion of the deformable material 150 may be determined by measuring a resistance through the deformable material 150. The resistance may be determined by, for example, coupling the deformable material 150 to at least a first electrode 154 (FIG. 2A) and at least a second electrode 154, applying a current between the electrodes 154, and measuring the resistance through the deformable material 150. Accordingly, in some embodiments, an amount of expansion or compression of the deformable material 150 may be determined based, at least in part, on an electrical resistance through the deformable material 150.

In other embodiments, water ingress into a portion of the wellbore 110 (FIG. 1) may be determined based on at least one measured electrical property of the deformable material 150. In some such embodiments, the deformable material 150 (FIG. 2A) may comprise, for example, a water-swellable material, as described above. Responsive to exposure to an aqueous solution (e.g., water, brine, etc.), the deformable material 150 may expand and, therefore, may exhibit an increased electrical resistance. Accordingly, water ingress from the subterranean formation may be detected or determined by measuring the resistance through the deformable material 150. In some embodiments, an increasing resistance through the deformable material 150 may correspond to water ingress into the wellbore 110 proximate the deformable material 150.

Although the packer device 138 (FIG. 1) has been illustrated as being disposed on an outer wall of the tubular member 122, the disclosure is not so limited. For example, in other embodiments, the packer device 138 may include at least a portion of a plug, such as a degradable plug, a frac plug (e.g., such as used in what is referred to in the art as "plug and perf" operations), a bridge plug, another device formulated to isolate one zone of the subterranean formation from another zone of the subterranean formation, another expandable downhole tool, or combinations thereof.

In some embodiments, the electronic device 158 may comprise a processor including a memory or may be coupled to the surface control unit 142 (FIG. 1) comprising a processor and a memory. The memory may store information related to, for example, a reference or baseline value of at least one electrical property (e.g., a resistance value) of the deformable material 150 in one or more different configurations or states (e.g., a compressed state, one or more partially expanded states, a fully expanded state, etc.). In some embodiments, the memory may be configured to store the information in the form of, for example, a look-up table including different values of at least one electrical property of the deformable material 150 while the deformable material 150 is at one or more different configurations. Responsive to receiving information about the at least one electrical property, the surface control unit 142 may estimate or determine one or more of a degree of expansion or contraction of the deformable material 150 or water ingress into the wellbore 110 proximate the deformable material 150 based, at least in part, on a value of the at least one electrical property or a difference between the reference value and the at least one measured value. In some embodiments, the surface control unit 142 may estimate or determine the degree of expansion or contraction of the deformable material 150 or water ingress into the wellbore 110 proximate the deformable material 150 in substantially real time.

The deformable material 150 may be formed by any suitable method for mixing the electrically conductive materials in the deformable material 150. In some embodiments, the deformable material 150 may be formed by mixing one or more electrically conductive materials with a deformable material to form a mixture and molding the mixture. The deformable material may cure around the electrically conductive materials to form a downhole article including the deformable material. In some embodiments, the deformable material 150 may be formed in a manner substantially similar to the manner disclosed in U.S. patent application Ser. No. 15/063,034, titled "DEFORMABLE DOWNHOLE STRUCTURES INCLUDING CARBON NANOTUBE MATERIALS, AND METHODS OF FORMING AND USING SUCH STRUCTURES," filed Mar. 7, 2016, the entire disclosure of which is incorporated herein in its entirety by this reference.

Figure 5:
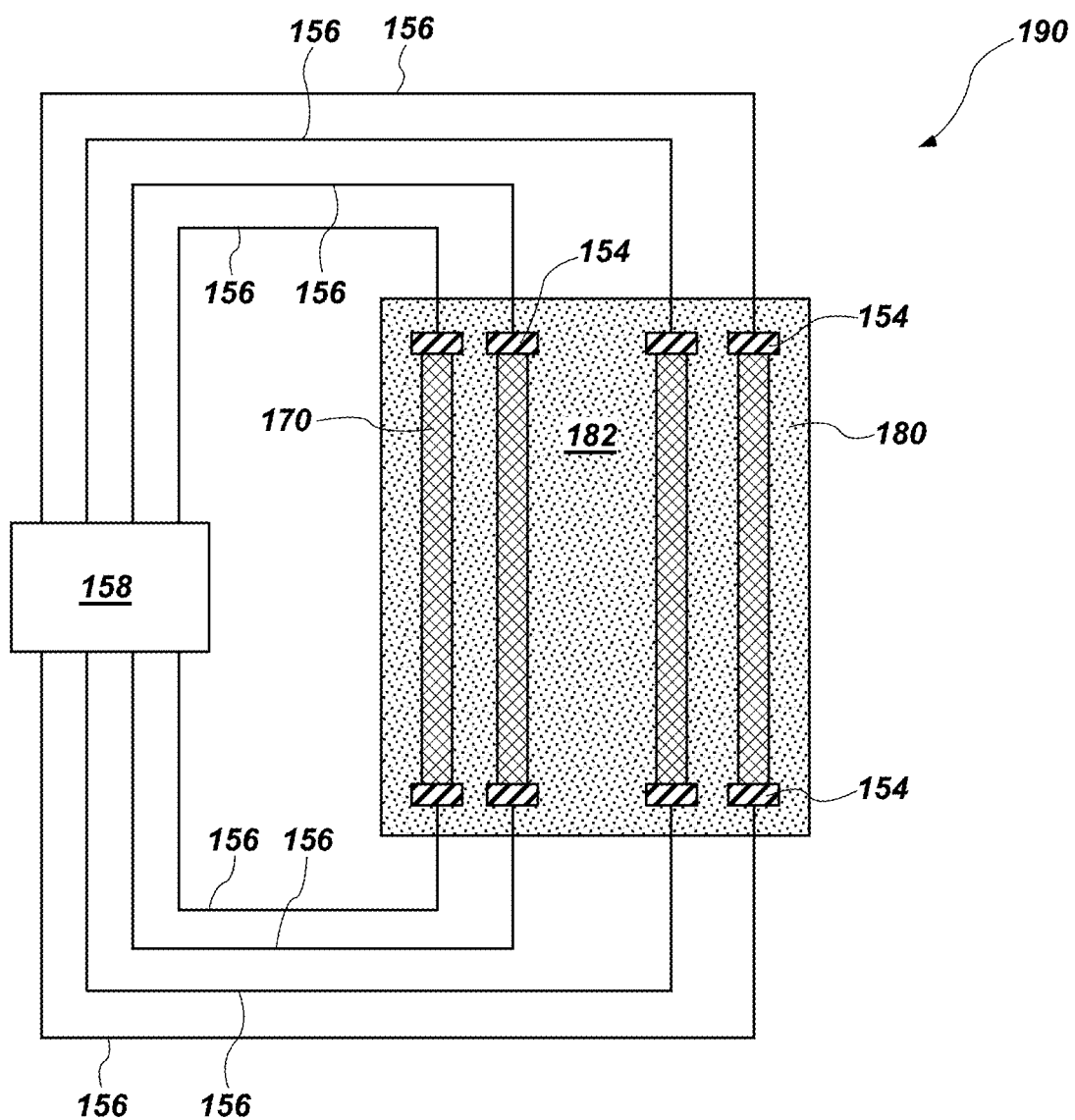
FIG. 5 is a cross-sectional side view of a degradable material including a plurality of electrically conductive elements therein, according to other embodiments of the disclosure.

In yet other embodiments, at least one downhole component or downhole article may comprise a degradable material. An amount of degradation of the degradable material may be determined based on one or more electrical properties of the degradable material. FIG. 5 illustrates a degradable downhole article 190 including a degradable material 180 including a plurality of electrically conductive elements 170 disposed therein. Each of the electrically conductive elements 170 may be in electrical communication with the electronic device 158 through one or more wires 156 and one or more electrodes 154 coupled thereto. The degradable downhole article 190 may comprise, by way of nonlimiting example, at least a part of a frac plug, a degradable plug (e.g., a degradable frac plug), a dissolvable plug, a bridge plug, a downhole valve, a flow controller, a degradable coating on a downhole tool, or another material formulated and configured to degrade, corrode, erode, or otherwise deteriorate. The degradable material 180 may include a polymer, a rubber, a paint, or other degradable materials. In some embodiments, the degradable material 180 includes a polymer or a rubber, as described above with reference to the deformable material 150. In yet other embodiments, the degradable material 180 comprises a controlled electrolytic material, a gel, a viscous fluid, or other suitable material that may degrade, corrode, erode, or otherwise deteriorate chemically, physically, or by any other means responsive to exposure to a downhole environment or stimulus.

The electrically conductive elements 170 may include a network of electrically conductive nanomaterials, such as carbon nanotubes or other electrically conductive material. In some embodiments, the electrically conductive elements 170 each comprise at least one carbon nanotube mat. The electronic device 158 may be configured to detect at least one electrical property of each of the electrically conductive elements 170. In some embodiments, each electrically conductive element 170 forms a circuit with the electronic device 158. In some embodiments, regions 182 of the degradable material 180 may be substantially free of the electrically conductive material (e.g., the electrically conductive elements 170) and may, therefore, be substantially electrically non-conductive (i.e., insulative).

In use and operation, the degradable material 180 may degrade. As the degradable material 180 degrades, one or more of the electrically conductive elements 170 may detach from the degradable material 180. The electrically conductive elements 170 may exhibit a difference in at least one electrical property when the electrically conductive element 170 is secured to the degradable material 180 than when the electrically conductive element 170 detaches therefrom. For example, in some embodiments, after an electrically conductive element 170 detaches from the degradable material 180, a circuit between the electronic device 158 and the degradable material 180 may break and the electronic device 158 may not detect the at least one electrical property. Accordingly, the electronic device 158 may be configured to determine a presence of each of the electrically conductive elements 170 in the degradable material 180. Stated another way, the electronic device 158 may be configured to determine whether each individual electrically conductive element 170 is disposed in the degradable material 180 or whether the degradable material 180 has degraded and an electrically conductive element 170 is detached therefrom.

The electrically conductive elements 170 may comprise, for example, an array of electrically conductive elements 170 positioned within the degradable material 180 at predetermined locations within the degradable material 180. In some embodiments, each of the electrically conductive elements 170 may be positioned at a different radial distance from a center of the degradable material 180. By way of nonlimiting example, a first electrically conductive element 170 may be positioned at a predetermined radial distance from a center of the degradable material 180, a second electrically conductive element 170 may be positioned at another predetermined radial distance from the center of the degradable material 180, and a third electrically conductive element 170 may be positioned at yet another predetermined radial distance from the center of the degradable material 180. In other embodiments, the electrically conductive elements 170 may be positioned and spaced along, for example, a longitudinal axis of the degradable material 180.

In some embodiments, the electrically conductive elements 170 may be positioned within the degradable material 180 such that degradation of the degradable material 180 may be determined in, for example, intervals of about 5%, about 10%, about 20%, about 25%, or other intervals. In other words, the electrically conductive elements 170 may be positioned within the degradable material 180 such that after the degradable material 180 degrades by a predetermined amount (e.g., 5%, 10%, 15%, 20%, etc.), an electrically conductive element 170 detaches therefrom and is, therefore, not detected by the electronic device 158. In some embodiments, the degradable material 180 is configured such that at least one electrically conductive element 170 detaches from the degradable material 180 after every about 5%, every about 10%, every about 20%, or every about 25% of the degradable material 180 has degraded. However, the disclosure is not so limited and degradation of the degradable material 180 may be estimated or determined at intervals of about 1%, about 2%, about 3%, or other intervals.

Forming the degradable material 180 including the electrically conductive elements 170 disposed at predetermined locations within the degradable material 180 facilitates determination of an amount of degradation of the degradable material 180. For example, only certain portions of the degradable material 180 may conduct electricity (e.g., the electrically conductive elements 170). Since each electrically conductive element 170 is positioned at predetermined locations of the degradable material 180, detection of an electrical property of the electrically conductive material 170 may provide an indication of the location of the electrically conductive material 170 relative to the degradable material 180.

In some embodiments, the memory of the electronic device 158 may store information related to, for example, a relative location of each electrically conductive element 170 within the degradable material 180. The electronic device 158 may be configured to determine an amount of degradation of the degradable material 180. By way of nonlimiting example, if the electronic device 158 does not detect the at least one electrical property of an electrically conductive element 170, the electronic device 158 may determine that the degradable material 180 has degraded by an amount corresponding to a location of the electrically conductive element 170. Responsive to receiving information about the at least one electrical property, the surface control unit 142 may determine or estimate an amount of degradation of the deformable material 150 in substantially real time.

The degradable material 180 may be formed by any suitable method for mixing the electrically conductive elements 170 (FIG. 5) in the degradable material 180. In some embodiments, the degradable material 180 may be formed by mixing a matrix material comprising a degradable material with one or more electrically conductive elements 170 and molding the mixture to form a degradable material. In some embodiments, one or more electrically conductive elements 170 may be positioned at predetermined positions within a mold cavity and the mold cavity may be filled with the degradable material. The degradable material may cure around the electrically conductive elements 170 to form a downhole article including the degradable material.

Additional nonlimiting example embodiments of the present disclosure are set forth below.

Embodiment 1

A method of determining a condition within a wellbore or a downhole article, the method comprising: introducing a tubular member in a wellbore extending through a subterranean formation, the tubular member comprising a downhole article including a deformable material disposed over a surface of the tubular member, the deformable material having electrically conductive nanomaterials dispersed therein; measuring at least one electrical property of the deformable material; and determining at least one of water ingress into the wellbore or an amount of expansion of the deformable material based on a value of the at least one measured electrical property.

Embodiment 2

The method of Embodiment 1, wherein measuring at least one electrical property of the deformable material comprises measuring an electrical resistance of the deformable material.

Embodiment 3

The method of Embodiment 1 or Embodiment 2, further comprising selecting the electrically conductive nanomaterials to comprise carbon nanotubes comprising a plurality of carbon nanotube mats, each carbon nanotube mat electrically coupled to a pair of electrodes.

Embodiment 4

The method of any one of Embodiments 1 through 3, wherein determining at least one of water ingress into the wellbore or amount of expansion of the deformable material based on the at least one measured electrical property comprises determining water ingress into the wellbore and an amount of expansion of the deformable material based on the at least one measured electrical property.

Embodiment 5

The method of any one of Embodiments 1 through 4, further comprising selecting the electrically conductive nanomaterials to comprise carbon nanotubes doped with metal nanoparticles.

Embodiment 6

The method of any one of Embodiments 1, 2, 4, or 5, further comprising selecting the deformable material to comprise carbon nanotubes dispersed substantially uniformly throughout the deformable material.

Embodiment 7

The method of any one of Embodiments 1 through 6, further comprising selecting the deformable material to comprise a water-swellable material.

Embodiment 8

The method of Embodiment 7, wherein the water-swellable material comprises carboxymethyl cellulose.

Embodiment 9

The method of any one of Embodiments 1 through 8, wherein introducing a tubular member in a wellbore extending through a subterranean formation comprises disposing the tubular member proximate an aquifer in the subterranean formation.

Embodiment 10

The method of any one of Embodiments 1 through 9, further comprising selecting the deformable material to comprise a shape memory polymer.

Embodiment 11

The method of any one of Embodiments 1 through 10, further comprising selecting the tubular member to comprise at least a portion of at least one of a bridge plug, a frac plug, a swellable packer, or a sand screen.

Embodiment 12

A downhole system for determining at least one condition within a wellbore, the downhole system comprising: a tubular member in a wellbore extending through a subterranean formation; a deformable material disposed over a surface of the tubular member, the deformable material comprising electrically conductive nanomaterials dispersed therein; at least one electronic device electrically coupled to electrodes within the deformable material, the electronic device configured to measure at least one electrical property of the deformable material; and a processor operably coupled to the at least one electronic device, the processor comprising a memory programmed to determine at least one of water ingress into the wellbore or an amount of expansion of the deformable material based on a value of the at least one measured electrical property.

Embodiment 13

The downhole system of Embodiment 12, wherein the tubular member comprises at least one of a frac plug, a bridge plug, a swellable packer, or a sand screen.

Embodiment 14

The downhole system of Embodiment 12 or Embodiment 13, wherein the deformable material comprises a plurality of carbon nanotube mats, each carbon nanotube mat electrically coupled to a pair of electrodes.

Embodiment 15

The downhole system of any one of Embodiments 12 through 14, wherein the electrically conductive nanomaterials comprise carbon nanotubes including metal nanoparticles, and wherein the carbon nanotubes are functionalized with functional groups comprising at least one of an amine group, a carboxyl group, a hydroxyl group, or a thiol group.

Embodiment 16

A method of determining an amount of degradation of a downhole tool, the method comprising: positioning a tubular member in a wellbore, the tubular member comprising a degradable material disposed around a surface of the tubular member and comprising a plurality of electrically conductive elements therein; measuring at least one electrical property of each of the electrically conductive elements; and determining an amount of degradation of the degradable material based, at least in part, on a value of the at least one measured electrical property of each of the electrically conductive elements.

Embodiment 17

The method of Embodiment 16, further comprising selecting the degradable material to comprise the electrically conductive elements, each electrically conductive element disposed at a different radial location of the degradable material, an electrically non-conductive material disposed between adjacent electrically conductive elements of the plurality of electrically conductive elements.

Embodiment 18

The method of Embodiment 16 or Embodiment 17, wherein determining an amount of degradation of the degradable material comprises correlating a measured value of an electrical property of each of the electrically conductive elements of the plurality of electrically conductive elements to an amount of degradation of the degradable material.

Embodiment 19

The method of any one of Embodiments 16 through 18, further comprising: measuring an electrical resistance across each electrically conductive element of the plurality of electrically conductive elements; and determining an amount of degradation of the degradable material based on a magnitude of the electrical resistance across each electrically conductive element of the electrically conductive elements.

Embodiment 20

The method of any one of Embodiments 16 through 19, further comprising selecting the electrically conductive elements to comprise carbon nanotube mats.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of determining a condition within a wellbore or a downhole article, the method comprising:
   introducing a tubular member in a wellbore extending through a subterranean formation, the tubular member comprising a downhole article including a deformable material disposed over a surface of the tubular member, the deformable material having electrically conductive nanomaterials dispersed therein;
   measuring at least one electrical property of the deformable material with electrodes disposed within the deformable material; and
   determining at least one of water ingress into the wellbore or an amount of expansion of the deformable material based on a value of the at least one measured electrical property.

2. The method of claim 1, wherein measuring at least one electrical property of the deformable material comprises measuring an electrical resistance of the deformable material.

3. The method of claim 1, further comprising selecting the electrically conductive nanomaterials to comprise carbon nanotubes comprising a plurality of carbon nanotube mats, each carbon nanotube mat electrically coupled to a pair of electrodes.

4. The method of claim 1, wherein determining at least one of water ingress into the wellbore or an amount of expansion of the deformable material based on the at least one measured electrical property comprises determining water ingress into the wellbore and an amount of expansion of the deformable material based on the at least one measured electrical property.

5. The method of claim 1, further comprising selecting the electrically conductive nanomaterials to comprise carbon nanotubes doped with metal nanoparticles.

6. The method of claim 1, further comprising selecting the deformable material to comprise carbon nanotubes dispersed substantially uniformly throughout the deformable material.

7. The method of claim 1, further comprising selecting the deformable material to comprise a water-swellable material.

8. The method of claim 7, wherein the water-swellable material comprises carboxymethyl cellulose.

9. The method of claim 7, wherein introducing the tubular member in a wellbore extending through a subterranean formation comprises disposing the tubular member proximate an aquifer in the subterranean formation.

10. The method of claim 1, further comprising selecting the deformable material to comprise a shape memory polymer.

11. The method of claim 1, further comprising selecting the tubular member to comprise at least a portion of at least one of a bridge plug, a frac plug, a swellable packer, or a sand screen.

12. A downhole system for determining at least one condition within a wellbore, the downhole system comprising:
    a tubular member in a wellbore extending through a subterranean formation;
    a deformable material disposed over a surface of the tubular member, the deformable material comprising electrically conductive nanomaterials dispersed therein;
    at least one electronic device electrically coupled to electrodes within the deformable material, the at least one electronic device configured to measure at least one electrical property of the deformable material; and
    a processor operably coupled to the at least one electronic device, the processor comprising a memory configured to determine at least one of water ingress into the wellbore or an amount of expansion of the deformable material based on a value of the at least one measured electrical property.

13. The downhole system of claim 12, wherein the tubular member comprises at least one of a frac plug, a bridge plug, a swellable packer, or a sand screen.

14. The downhole system of claim 12, wherein the deformable material comprises a plurality of carbon nanotube mats, each carbon nanotube mat electrically coupled to a pair of electrodes.

15. The downhole system of claim 12, wherein the electrically conductive nanomaterials comprise carbon nanotubes including metal nanoparticles, and wherein the carbon nanotubes are functionalized with functional groups comprising at least one of an amine group, a carboxyl group, a hydroxyl group, or a thiol group.

16. A method of determining an amount of degradation of a downhole tool, the method comprising:
  positioning a tubular member in a wellbore, the tubular member comprising a degradable material disposed around a surface of the tubular member and comprising a plurality of electrically conductive elements therein;
  measuring at least one electrical property of each of the electrically conductive elements; and
  determining an amount of degradation of the degradable material based, at least in part, on a value of the at least one measured electrical property of each of the electrically conductive elements.

17. The method of claim 16, further comprising selecting the degradable material to comprise the electrically conductive elements, each electrically conductive element disposed at a different radial location of the degradable material, an electrically non-conductive material disposed between adjacent electrically conductive elements of the plurality of electrically conductive elements.

18. The method of claim 16, wherein determining an amount of degradation of the degradable material comprises correlating a measured value of an electrical property of each of the electrically conductive elements of the plurality of electrically conductive elements to an amount of degradation of the degradable material.

19. The method of claim 16, further comprising:
  measuring an electrical resistance across each electrically conductive element of the plurality of electrically conductive elements; and
  determining an amount of degradation of the degradable material based on a magnitude of the electrical resistance across each electrically conductive element of the electrically conductive elements.

20. The method of claim 19, further comprising selecting the electrically conductive elements to comprise carbon nanotube mats.

* * * * *